United States Patent [19]

Zengel et al.

[11] 4,307,236

[45] Dec. 22, 1981

[54] PROCESS FOR THE PREPARATION OF DITHIAZOLE-DISULFIDES

[75] Inventors: Hans Zengel, Kleinwallstadt; Manfred Bergfeld, Erlenbach, Mechenhard; Ludwig Eisenhuth, Elsenfeld, all of Fed. Rep. of Germany

[73] Assignee: Akzona Incorporated, Asheville, N.C.

[21] Appl. No.: 196,897

[22] Filed: Oct. 14, 1980

[30] Foreign Application Priority Data

Nov. 2, 1979 [DE] Fed. Rep. of Germany ....... 2944225

[51] Int. Cl.³ .......................................... C07D 277/70
[52] U.S. Cl. ..................................... 548/158; 548/186
[58] Field of Search ........................ 548/158, 186, 183

[56] References Cited

U.S. PATENT DOCUMENTS

| | | | |
|---|---|---|---|
| 3,086,018 | 4/1963 | Hardman | 548/186 |
| 3,463,783 | 8/1969 | Strauss et al. | 548/186 |
| 3,925,401 | 12/1975 | Janin | 548/186 |
| 4,143,045 | 3/1979 | Tazuma et al. | 548/158 |

*Primary Examiner*—Nicholas S. Rizzo
*Attorney, Agent, or Firm*—Francis W. Young; Steven M. Odre; Robert F. Green

[57] ABSTRACT

This disclosure relates to a novel process for preparing a class of dithiazolyl-(2,2')-disulfides by the catalytic oxidation of 2-mercaptothiazoles. In particular the present invention involves a process for preparing dibenzothiazyl-disulfides upon the oxidation of a 2-mercaptobenzothiazole in the presence of a tertiary amine.

7 Claims, No Drawings

PROCESS FOR THE PREPARATION OF DITHIAZOLE-DISULFIDES

The present invention relates to a novel process for the preparation of a class of dithiazolyl-(2,2')-disulfides by the catalytic oxidation of 2-mercaptothiazoles. In particular the present invention involves the preparation of dibenzothiazyl disulfides upon the oxidation of a 2-mercaptobenzothiazole in the presence of a tertiary amine.

Heretofore, different oxidating agents have been used in the industrial preparation of dibenzothiazyl-disulfides. According to a process described in the FIAT Final Report 1018, p. 22 (cf. also BIOS Final Report 661, p. 8, and Ullmann's Encyclopedia of Industrial Chemistry, 3rd edition, vol. 12, p. 308, Urban & Schwarzenberg, publishers, Munich and Berlin, 1960), the reaction is carried out with sodium chlorate and sodium nitrite solution in a hydrochloric medium at 30° C. However, there are disadvantages associated with this process. The consumption of mineral acid is very high (3 mols of HCl per mol of 2-mercaptobenzothiazole) and large quantities of by-products are formed, namely 34 kg of common salt per 100 kg of dibenzothiazyl-disulfide, as well as nitric oxides. In addition, undesirable by-products are formed by peroxidation. Another known process involves the oxidation of the 2-mercaptobenzothiazole utilizing nitrous acid. According to the process described in U.S. Pat. No. 1,908,935, 2-mercaptobenzothiazole is suspended in water, a water-soluble nitrite, e.g. an alkali or ammonium nitrite, is added, and oxygen, or an oxygen-containing gas, such as air, is conducted through the reaction mixture. Simultaneously, a mineral acid liberating nitrous acid from the nitrite is added. The reaction takes place at temperatures between 50° C. and 100° C. In this process, nitrite is used in quantities of only 5 to 40% of the quantity theoretically required for the oxidation of the mercapto compound to the disulfide, while the oxygen has the task of regenerating the nitric oxide to nitrous acid. In the processes described in U.S. Pat. No. 2,119,131 and U.S. Pat. No. 3,062,825, stoichiometric quantities of nitrite are used as the only oxidating agent. This accomplishes a more rapid and more complete conversion. However, these oxidation processes also have disadvantages, namely, the consumption of mineral acid is very high and salts, and nitric oxides are obtained in large quantities as by-products.

In addition, chlorine has been used as an oxidizing agent (Kirk-Othmer, Encyclopedia of Polymer Science and Technology (1970), vol. 12, p. 262). However when chlorine is employed as the oxidizing agent a complicated reaction with critical reaction conditions is involved. According to a recent procedure, described in German patent application disclosure No. 23 09 584, separate streams of an aqueous solution of an alkali metal salt of mercaptobenzothiazole, an aqueous solution of an alkali metal hydroxide, and gaseous chlorine are continuously reacted with each other below the surface of the liquid at 20° C. to 75° C. and with vigorous stirring, in order to increase the yield of product and to reduce the quantity of excess chlorine required for an adequate oxidation. The pH value and the redox potential of the aqueous mixture are held at a pH of 7-10 and at a redox potential from $-150$ to 250 mV by regulating the feed of the aqueous hydroxide solution and of the gaseous chlorine. In addition this procedure requires very careful control in order to prevent the continued oxidation of the dibenzothiazyl-disulfide to benzothiazyl-2-sulfinate and -sulfonate. Disadvantages associated with this procedure include the fact that large quantities of alkali hydroxide are consumed and large quantities of common salt are formed as by-product.

Hydroperoxides, such as hydrogen peroxide, alkali hydroperoxides and aralkyl hydroperoxides have also been used already as oxidating agents in the preparation of dibenzothiazyl-disulfide. According to the procedure described in German patent application disclosure No. 23 49 314, oxidation takes place in the solution of a saturated, aliphatic alcohol containing 1 to 4 carbon atoms, preferably methyl or isopropyl alcohol and preferably using hydrogen peroxide and at temperatures between 0° C. and 100° C., but not above the boiling point of the alcohol (cf. alco Chem. Abstr., vol. 87 (1977) 23129j). Since 2-mercaptobenzothiazole can readily be dissolved in the mentioned alcohols, whereas dibenzothiazyldisulfide will dissolve very little, this oxidation procedure can be carried out very simply. When the hydroperoxide is added, the reaction product will precipitate immediately from the clear 2-mercaptobenzothiazole solution, and is obtained in pure form by means of simple filtration. The initial alcohol solution may contain up to 20% of water. Under these conditions one obtains satisfactory yields and selectivities at high reaction temperatures, whereas at room temperature one achieves unchanged, high selectivities, but only low conversion rates. According to the procedure of the published Japanese patent application No. 74-82659 (cf. Chem. Abstr., vol. 82 (1975), 156271 Z), oxidation of the 2-mercaptobenzothiazole takes place in the presence of finely powdered dibenzothiazyl-disulfide and/or an anionic surfactant, e.g. polyethyleneglycol ether and sodium alkyl benzene sulfonate.

However, in all of the above-mentioned oxidation procedures comparatively expensive oxidating agents and acids, bases, or other auxiliary materials are required, and partly unusable by-products are obtained.

It should be noted that a procedure for the electrolytic oxidation of 2-mercaptobenzothiazole to dibenzothiazyl-disulfide (German patent application disclosure No. 27 43 629) and a procedure wherein ozone is used as oxidating agent (USSR Pat. No. 420,247) are known in the art.

It has also been investigated, whether oxidation of the 2-mercaptobenzothiazole to dibenzothiazyl-disulfide can be carried out with oxygen as the only oxidizing agent. According to the procedure described in U.S. Pat. No. 3,654,297, this is possible if cobalt phthalocyanin sulfate, disulfonate, trisulfonate or tetrasulfonate, or mixtures of these, are employed as catalyst, and the oxidation is carried out in an organic solvent containing less than 15% by weight of water, at temperatures of 50° to 80° C. (cf. also USSR Pat. No. 575,348; Chem. Abstr. 88 (1978), 89657 g). However, preparation and industrial application of this catalyst are difficult.

Finally, German patent application disclosure No. 23 55 897 describes the oxidation of 2-mercaptobenzothiazoles to dibenzothiazyl-disulfides using oxygen, or a gas containing oxygen, and iron chloride, in particular iron (III) chloride, in a saturated, aliphatic alcohol containing 1 to 10 carbon atoms at temperatures between 0° C. and 150° C. However, the catalyst employed in this procedure will produce satisfactory reaction rates only if it is used in larger quantities, namely in a ratio of 0.8 to 1.5 mol per mol of 2-mercaptobenzothiazole. The disadvantage of this procedure is that the iron precipitates during the reaction in the form of basic salts, and the obtainable dibenzothiazyl-disulfide is badly contaminated with iron. Therefore a product obtained in this manner cannot be used as a vulcanizing agent without expensive purification.

Consequently, there exists a need for the development of a procedure for the catalytic oxidation of 2-mercaptobenzothiazole using oxygen, or gases containing oxygen.

The subject of the present invention is a procedure for the preparation of a class of dithiazolyl-(2,2')-disulfides of the general formula

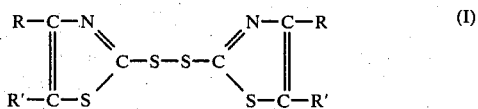  (I)

wherein R and R' are independently selected from the group consisting of hydrogen, halogen, nitro, hydroxyl and substituted $C_1$–$C_6$ alkyl, $C_1$–$C_6$ alkoxy, $C_6$–$C_{12}$ cycloalkyl or $C_6$–$C_{12}$ aryl containing one or more substituents selected from the class consisting of halogen, nitro, $C_1$–$C_5$ alkyl and $C_1$–$C_5$ alkoxy; or R and R' jointly may form the substituent

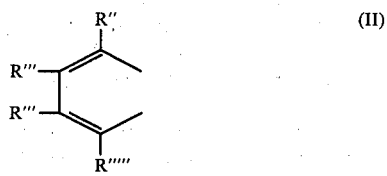  (II)

whereby R'', R''', R'''' and R''''' are independently selected from the groups represented by R and R', which comprises catalytically oxidizing a 2-mercaptothiazole of the general formula

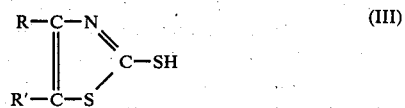  (III)

utilizing oxygen, or a gas containing oxygen, in the presence of a solvent at temperatures in a range from 0° C. to 150° C., in the presence of a tertiary amine catalyst and, optionally, a heavy metal or a heavy metal compound as a cocatalyst.

Preferably, substituents R, R', R'', R''', R'''' and R''''' of the general formulae, I, II and III are a chlorine or bromine atom, a hydroxyl group, a nitro group, an alkyl group with straight chain or branched chain having 1 to 4 carbon atoms, such as methyl, ethyl, propyl, isopropyl, butyl or t-butyl, an alkoxy group with 1 to 4 carbon atoms, such as methoxy, ethoxy, propoxy or butoxy, or a phenyl, tolyl, ethylphenyl, nitrophenyl, chlorophenyl, bromophenyl or naphthyl group.

The dithiazolyl-(2,2')-disulfides of the present invention are used as vulcanizing agents for rubber. The process of the present invention is of particular importance in the preparation of dibenzothiazolyl-(2,2')-disulfide. In addition the process of the present invention may be used successfully for the preparation of additional dithiazolyl-(2,2')-disulfides. 2-mercaptobenzothazole is used as initial material for the preferred preparation of dibenzothiazolyl-(2,2')-disulfide. Examples of other 2-mercaptothiazoles suitable as starting materials for the preparation of dithiazolyl-(2,2')-disulfides of general formula I include, for example, the compounds mentioned in German patent application disclosure No. 23 55 897, such as:

2-mercaptothiazole
2-mercapto-4-methylthiazole
2-mercapto-4-ethylthiazole
2-mercapto-4n-propylthiazole
2-mercapto-4n-butylthiazole
2-mercapto-4,5-dimethylthiazole
2-mercapto-4,5-di-n-butylthiazole
2-mercapto-4-phenylthiazole
2-mercapto-5-chloro-4-phenylthiazole
2-mercapto-4-p-bromophenylthiazole
2-mercapto-4-m-nitrophenylthiazole
2-mercapto-4-m-chlorophenylthiazole
2-mercapto-4-methylbenzothiazole
2-mercapto-5-methylbenzothiazole
2-mercapto-6-methylbenzothiazole
2-mercapto-4,5-dimethylbenzothiazole
2-mercapto-4-phenylbenzothiazole
2-mercapto-4-methoxybenzothiazole
2-mercapto-6-methoxybenzothiazole
2-mercapto-5,6-dimethoxybenzothiazole
2-mercapto-6-methoxy-4-nitrobenzothiazole
2-mercapto-6-ethoxybenzothiazole
2-mercapto-4-chlorobenzothiazole
2-mercapto-5-chlorobenzothiazole
2-mercapto-6-chlorobenzothiazole
2-mercapto-7-chlorobenzothiazole
2-mercapto-5-chloro-6-methoxybenzothiazole
2-mercapto-5-chloro-4-nitrobenzothiazole
2-mercapto-5-chloro-6-nitrobenzothiazole
2-mercapto-4,5-dichlorobenzothiazole
2-mercapto-4,7-dichlorobenzothiazole
2-mercapto-5-nitrobenzothiazole
2-mercapto-6-nitrobenzothiazole
2-mercapto-4-phenylbenzothiazole
2-mercapto-naphthothiazole
2-mercapto-6-hydroxybenzothiazole.

It has been surprisingly found, that tertiary amines catalyze the oxidation of 2-mercaptothiazoles to dithiazolyl-(2,2')-disulfides. Suitable tertiary amines include aliphatic, cycloaliphatic, aromatic and heterocyclic amines, such as trimethylamine, triethylamine, tri-n-propylamine, tri-n-butylamine, n-octyl-dimethylamine, diisopropyl-ethylamine, propyl-dimethylamine, ethyl-dimethylamine, isopropyl-dimethylamine, butyl-dimethylamine, pyridine, N-methylpyridine, N-methylpyrrolidine, 2,4,6-trimethyl-pyridine, 2,3,4,5-tetramethyl-pyridine, 2,3,4,5,6-pentamethyl-pyridine, dimethyl-aniline, 4-dimethylamino-pyridine, 1,4-diazobicyclo-(2,2,2)-octane. Preferred tertiary amines are trimethylamine, triethylamine, tri-n-propylamine and tri-n-butylamine.

The quantity of tertiary amine can be varied within a wide range. Catalytic quantities are generally sufficient. The catalytic effectiveness increases with increasing quantities of the tertiary amine. The concentration of tertiary amine in the reaction mixture is of greater importance than the ratio of tertiary amine to the mercaptothiazole used. Preferably, the tertiary amine is employed in quantities of 0.1 to 20% by weight, of the reaction mixture.

The tertiary amines used according to the process of the present invention can be used alone, as well as together with a cocatalyst such as a heavy metal or a heavy metal compound. Suitable cocatalysts include for example, heavy metals such as iron, cobalt, nickel, copper, chrome, zinc, manganese and silver; metal oxides, as well as heavy metal inorganic or organic salts and complex compounds. It has been surprisingly found that copper and copper compounds, when employed together with a tertiary amine, have a particularly pronounced catalytic effectiveness. Therefore, copper, or a copper compound, is preferably used in addition to a tertiary amine, and preferably in quantities of less than 0.1% by weight, of the 2-mercaptothiazole. This corresponds to less than 10 mg of copper, or copper compound, per 10 g of the mercaptothiazole. Since traces of a copper cocatalyst display considerable catalytic activity and lead to good dithiazolyl-disulfide yields, it is thus possible, surprisingly, to use small catalyst quantities and to circulate the mother liquor repeatedly without having to accept a decline in reaction rate. For example, after 10 reaction cycles with the same mother liquor and without addition of fresh copper catalyst no decline in catalyst activity was observed.

Copper, as well as copper compounds, are suitable as copper cocatalyst. Since, with respect to the 2-mercaptobenzothiazole, the copper compound is used in such small quantities, not only may easily soluble copper compounds be employed, but also copper compounds with very low solubility, or those of which only trace amounts are soluble in the solvent are suitable. As a copper compound cocatalyst, one can consider all mono- divalent inorganic, organic, simple, or complex copper salts. Examples of suitable monovalent copper salts include copper (I) chloride, bromide and iodide, addition compounds of these copper (I) halides with carbon monoxide, complex copper (I) salts such as the alkalichlorocuprates, complex ammoniates of copper (I) cyanide, e.g. cyanocuprates such as potassium tricyanocuprate (I), double salts with copper (I) rhodanide, copper (I) acetate, copper (I), sulfite and complex double sulfides of copper (II) salts are copper (II) chloride, bromide, sulfide, sulfate, nitrate, nitrite, rhodanide, cyanide, copper (II) salts of carboxylic acids, such as copper (II) acetate, as well as the complex ammoniates of copper (II) salts. Metallic copper and copper (I) oxide are also very well suited as cocatalyst. Preferably, powdered copper, copper (I) chloride, copper (II) acetate, copper (II) sulfate, copper (II) oleate, copper (II) acetylacetonate, copper (II) sulfide, or copper (I) oxide is employed as a cocatalyst.

Suitable solvents include oxidation-resistant organic solvents such as, for examples, alcohols, dimethyl formamide, benzene, toluene and chlorobenzene. Suitable alcohols include, for example, aliphatic alcohols containing 1 to 10 carbon atoms, in particular methanol, ethanol, propanol, isopropanol, sec. butanol, tert. butanol, pentanol, isopentanol, tert. pentanol, hexanol, heptanol and octanol. Preferably, toluene and isopropanol are employed as solvents. The concentration of the solvent is not critical. In general, a quantity of solvent in a range from 200 to 1200% by weight, with respect to the 2-mercaptothiazole is used. Greater quantities of solvent should be avoided for economic reasons, as larger quantities of tertiary amine are then required.

Oxygen or a gas containing oxygen, preferably air is employed as an oxidizing agent. Conversion level and selectivity increase with increasing oxygen pressure, or partial pressure. In general, an oxygen pressure, or partial pressure, of 2 to 10 bar is preferred.

The reaction temperature is 0° C. to 150° C., preferably 20° C. to 90° C., and in particular 60° C. to 80° C. At lower temperatures, there is a decline in reaction rate, at higher temperatures a decline in the selectivity of the reaction.

As a rule, the duration of the reaction is 0.5 to 6.5 hours; under the mentioned preferred pressure and temperature conditions, and in the presence of a copper cocatalyst it is less than an hour at an 80% conversion rate.

The process of the present invention involves conducting the oxygen, or oxygen-containing gas, under the indicated pressure and temperature conditions, into, or through a solution consisting of 2-mercaptothiazole, solvent, copper catalyst and tertiary amine. Since unconverted 2-mercaptothiazole, if any, remains dissolved in the solvent, processing of the reaction mixture becomes relatively simple. The precipitated reaction product is filtered, or centrifuged off, the mother liquor is mixed with fresh 2-mercaptothiazole and recirculated. Depending upon the level of the initial concentration of copper catalyst, fresh catalyst may be added after a certain number of reaction cycles. In addition, the water of reaction formed during the conversion should be removed from the mother liquor when its content, with respect to the mother liquor, amounts to more than 10% by weight.

Quantitative yields and selectivities of more than 99% are obtained in the process of the present invention. The dithiazolyl-(2,2')-disulfides produced in accordance with the process of the present invention possess high purity and can therefore be used directly as rubber vulcanizing agents without any further purification. Compared with the two known processes, in which a 2-mercaptobenzothiazole is oxidized using oxygen, the process of the present invention is distinguished by the fact that simple and cheap catalysts are used in very small quantities, and that these catalysts can be circulated with the mother liquor without any noticeable decline in their activity.

EXAMPLE 1

40 g. (240 mmol) of 2-mercaptobenzothiazole (MBT), 4 mg. (0.02 mmol) of copper (II) acetate, 10.9 g. (108 mmol) triethylamine and 120 g. of isopropanol were placed in a 500 ml glass autoclave equipped with a double wall for the circulation of a heating liquid, a thermometer, a pressure measuring device and a stirring device. Gas was extracted from the reactor, the reaction mixture was heated to 70° C., and oxygen was then applied under a pressure of 2 bar.

The initially clear solution began to become turbid after only a few minutes. After 6.5 hours the reaction was terminated, the precipitate filtered off, washed with isopropanol, and dried under a vacuum.

38.2 g. of dibenzothiazyl disulfide (MBTS) was obtained and the purity was found by chromatographic analysis to be 100%.

After concentration by means of extractive separation with methanol, an additional 0.4 g. of dibenzothiazyl-disulfide was isolated from the filtrate. In addition, the quantity of unreacted 2-mercaptobenzothiazole in the residue was determined to be 0.8 g. by potentiometric titration with aqueous silver nitrate solution. Thus, the yield of dibenzothiazyl-disulfide was 97.1% at a 2-mercaptobenzothiazole conversion of 98.0%. The selectivity of the reaction was calculated to be 99.1%.

EXAMPLE 2

Employing the procedure of Example 1, but without the addition of copper (II) acetate, and at an oxygen pressure of 9.0 bar, it was possible to isolate 33.4 g. of dibenzothiazyl-disulfide after a reaction period of 6.5 hours. The unreacted mercaptobenzothiazole was found to be 5.76 g. The yield of dibenzothiazyl-disulfide was 83.9% at a mercaptobenzothiazole conversion of 85.6%.

EXAMPLE 3

The procedure of Example 1 was employed, but without the addition of triethylamine. After 6.5 hours there was no change in the reaction mixture and no precipitate formed. Only unreacted mercaptobenzothiazole was found in the solution. This example shows, that it is not possible to oxidize mercaptobenzothiazole to dibenzothiazyl-disulfide of oxygen in the absence of a tertiary amine catalyst.

EXAMPLES 4 TO 11

Employing the procedure described in Example 1, 10 g. (60 mmol) of 2-mercaptobenzothiazole were oxidized using 4 mg (0.02 mmol) of copper (II) acetate, 108 mmol of a tertiary amine in 120 g. of isopropanol at 70° C. and at an oxygen pressure of 2.0 bar. The results obtained after a reaction period of 6.5 hours, with various amines, are compiled in Table 1. The following abbreviations are hereinafter used in the following Tables:

MBT: mercaptobenzothiazole
MBTS: dibenzothiazyl disulfide

TABLE 1

| Example | Amine (108 mmol) | MBT (mmol) | MBT Conversion (%) | MBTS Yield (%) |
|---|---|---|---|---|
| 4 | triethylamine | 60 | 82.7 | 80.5 |
| 5 | trimethylamine | 60 | 50.1 | 48.6 |
| 6 | tri-n-butylamine | 60 | 13.5 | 13.0 |
| 7 | n-octyl-dimethylamine | 60 | 43.5 | 42.1 |
| 8 | diisopropyl ethylamine | 60 | 53.5 | 52.1 |
| 9 | N-methyl pyridine | 60 | 47.7 | 46.0 |
| 10 | 1,4-diazobicyclo-(2,2,2)-octane | 60 | 24.5 | 23.6 |
| 11 | 4-dimethylaminopyridine | 60 | 66.0 | 64.1 |

EXAMPLES 12 TO 17

Employing the procedure described in Example 1, 10 g. (60 mmol) of mercaptobenzothiazole were oxidized using 4 mg (0.02 mmol) of copper (II) acetate, employing varying quantities of triethylamine in 120 g. of isopropanol, at 70° C. and at an oxygen pressure of 2.0 bar. The results obtained upon varying the quantity of triethylamine, after a reaction period of 6.5 hours, are compiled in Table 2.

TABLE 2

| Example | MBT (mmol) | Triethylamine (mmol) | MBT Conversion (%) | MBTS Yield (%) |
|---|---|---|---|---|
| 12 | 60 | 0 | 0 | 0 |
| 13 | 60 | 7.2 | 31.1 | 30.2 |
| 14 | 60 | 108 | 82.7 | 80.5 |
| 15 | 60 | 360 | 50.4 | 48.9 |
| 16 | 240 | 108 | 98.0 | 97.1 |
| 17 | 240 | 432 | 53.2 | 52.1 |

EXAMPLES 18 TO 25

Employing the procedure described in Example 1, 10 g. (60 mmol) of 2-mercaptobenzothiazole were oxidized with 4 mg (0.02 mmol) of copper (II) acetate, 10.9 g. (108 mmol) of triethylamine, in 120 g. of various solvents, at 70° C. and at an oxygen pressure of 2.0 bar. The results obtained varying the type of solvent, after a reaction period of 6.5 hours, are compiled in Table 3.

TABLE 3

| Example | Solvent, 120 g. | MBT (mmol) | MBT Conversion (%) | MBTS Yield (%) |
|---|---|---|---|---|
| 18 | isopropanol | 60 | 82.7 | 80.5 |
| 19 | n-propanol | 60 | 11.8 | 11.3 |
| 20 | ethanol | 60 | 61.0 | 59.5 |
| 21 | methanol | 60 | 32.1 | 31.2 |
| 22 | glycol | 60 | 17.8 | 17.3 |
| 23 | dimethyl foramide | 60 | 71.1 | 65.0 |
| 24 | toluene | 60 | 90.6 | 88.0 |
| 25 | chlorobenzene | 60 | 83.5 | 81.0 |

EXAMPLES 26 TO 35

As in Example 1, 10 g. (60 mmol) of 2-mercaptobenzothiazole were oxidized with 0.02 mmol of various copper compounds, 10.9 g. (108 mmol) of triethylamine in 120 g. of isopropanol, at 70° C. and at an oxygen pressure of 2.0 bar. The results obtained after a reaction period of 6.5 hours of reaction are compiled in Table 4.

TABLE 4

| Example | Copper compound | (mmol) | MBT (mmol) | MBT Conversion (%) | MBTS Yield (%) |
|---|---|---|---|---|---|
| 26 | copper(II) sulfate | (0.02) | 60 | 83.9 | 81.8 |
| 27 | copper(II) acetate | (0.02) | 60 | 82.7 | 80.5 |
| 28 | copper(II) oleate | (0.02) | 60 | 82.0 | 80.2 |
| 29 | copper(II) acetylacetonate | (0.02) | 60 | 81.2 | 79.8 |
| 30 | copper(II) sulfide | (0.02) | 60 | 63.6 | 61.9 |
| 31 | copper(I) oxide | (0.02) | 60 | 72.0 | 70.6 |
| 32 | copper(I) chloride | (0.02) | 60 | 77.6 | 76.0 |
| 33 | copper | (0.02) | 60 | 85.7 | 84.0 |
| 34 | copper(II) acetate | (0.02) | 60 | 86.7 | 84.5 |
| 35 | copper(II) acetate | (0.005) | 60 | 64.0 | 62.2 |
| 36 | no copper compound | | 60 | 45.4 | 44.3 |

EXAMPLES 37 TO 45

As in Example 1, 10 g. (60 mmol) of 2-mercaptobenzothiazole were oxidized using catalytic quantities of various heavy metal compounds, 10.9 g. (108 mmol) of triethylamine in 120 g. of isopropanol at 70° C. and at oxygen pressure of 2.0 bar. The results obtained after a reaction period of 6.5 hours are compiled in Table 5.

TABLE 5

| Example | MBT (mmol) | Metal compounds | (mmol) | MBT Conversion (%) | MBTS Yield (%) |
|---|---|---|---|---|---|
| 37 | 60 | cobalt(II) sulfate | (0.02) | 43.8 | 42.5 |
| 38 | 60 | cobalt(II) sulfate | (2.0) | 59.2 | 56.6 |
| 39 | 60 | manganese(II) acetate | (0.02) | 46.1 | 44.5 |
| 40 | 60 | manganese(II) acetate | (2.0) | 99.0 | 82.8 |
| 41 | 60 | iron(II) sulfate | (0.02) | 47.9 | 46.0 |
| 42 | 60 | nickel(II) sulfate | (0.02) | 43.0 | 41.3 |
| 43 | 60 | chrome(III) acetylcarbonate | (0.02) | 31.0 | 29.8 |

TABLE 5-continued

| Example | MBT (mmol) | Metal compounds (mmol) | | MBT Conversion (%) | MBTS Yield (%) |
|---|---|---|---|---|---|
| 44 | 60 | silver(I) acetate | (0.02) | 31.7 | 30.4 |
| 45 | 60 | tin stearate | (2.0) | 32.4 | 31.0 |

EXAMPLES 46 TO 48

As in Example 1, 10 g. (60 mmol) of 2-mercaptobenzothiazole were oxidized using 4 mg (0.02 mmol) of copper (II) acetate, 10.9 g. (108 mmol) of triethylamine in 120 g. of isopropanol, at 70° C., and at various oxygen pressures. The results of these experiments are compiled in Table 6.

TABLE 6

| Example | MBT (mmol) | Oxygen/Air | Reaction time (hr) | MBT Conversion (%) | MBTS Yield (%) |
|---|---|---|---|---|---|
| 46 | 60 | 0.8 bar (oxygen) | 6.5 | 47.3 | 46.1 |
| 47 | 60 | 10 bar (oxygen) | 2.5 | 70.9 | 70.3 |
| 48 | 60 | 4.5 bar (air) | 6.5 | 42.9 | 42.0 |

EXAMPLES 49 AND 50

As in Example 1, 10 g. (60 mmol) of 2-mercaptobenzothiazole were oxidized with 4 mg (0.02) of copper (II) acetate, 10.9 g. (108 mmol) of triethylamine, in 120 g. of isopropanol under an oxygen pressure of 2.0 bar, and varying the reaction temperature. The results of these experiments are compiled in Table 7.

TABLE 7

| Example | MBT (mmol) | Reaction temperature (°C.) | MBT Conversion (%) | MBTS Yield (%) |
|---|---|---|---|---|
| 49 | 60 | 92 | 63.9 | 45.5 |
| 50 | 60 | 20 | 5.0 | 4.8 |

What is claimed is:

1. A process for preparing a compound of the formula:

$$R-C=N\diagdown C-S-S-C \diagup N=C-R \atop R'-C-S \qquad\qquad S-C-R'$$

wherein R and R' are independently selected from the group consisting of hydrogen, halogen, nitro, hydroxyl and substituted $C_1$–$C_6$ alkyl, $C_1$–$C_6$ alkoxy, $C_6$–$C_{12}$ cycloalkyl or $C_6$–$C_{12}$ aryl containing one or more substituents selected from the class consisting of halogen, nitro, $C_1$–$C_5$ alkyl and $C_1$–$C_5$ alkoxy; or R and R' jointly may form the substituent $$R'''-\overset{R''}{\underset{R''''}{\diagdown}}$$

whereby R'', R''', R'''' and R''''' are independently selected from the groups represented by R and R', which comprises catalytically oxidizing a 2-mercaptothiazole of the general formula $$R-C=N\diagdown C-SH \atop R'-C-S \diagup$$

utilizing oxygen, or a gas containing oxygen, in the presence of a solvent at temperatures in a range from 0° C. to 150° C., in the presence of a tertiary amine catalyst.

2. A process according to claim 1 wherein the tertiary amine catalyst is selected from the class consisting of trimethylamine, triethylamine, tri-n-propylamine and tri-n-butylamine.

3. A process according to claim 2 wherein a tertiary amine is employed in quantities of 0.1 to 20% by weight of the reaction mixture.

4. A process according to claim 1 wherein a cocatalyst consisting of a heavy metal, or a heavy metal compound is employed.

5. A process according to claim 4 wherein the cocatalyst is copper or a copper compound.

6. A process according to claim 5 wherein a copper compound is employed in quantities of less than 0.1% by weight of 2-mercaptobenzothiazole.

7. A process according to claim 6 wherein a copper compound is selected from the class consisting of powdered copper, copper-(I)-chloride, copper-(II)-acetate, copper-(II)-sulfate, copper-(II)-oleate, copper-(II)-acetylacetonate, copper-(II)-sulfide, and copper-(II)-oxide.

* * * * *